United States Patent [19]

Slivenko

[11] 4,108,174

[45] Aug. 22, 1978

[54] CATHETER INTERLOCK SYSTEM

[75] Inventor: Victor Slivenko, San Diego, Calif.

[73] Assignee: General Atomic Company, San Diego, Calif.

[21] Appl. No.: 787,077

[22] Filed: Apr. 13, 1977

Related U.S. Application Data

[63] Continuation-in-part of Ser. No. 764,207, Jan. 31, 1977.

[51] Int. Cl.² ............................................. A61M 5/00
[52] U.S. Cl. .................................. 128/214 R; 128/348
[58] Field of Search ............... 128/214 R, 214 B, 348, 128/350 R, 1 R, 334 R, 274

[56] References Cited

U.S. PATENT DOCUMENTS

| | | | |
|---|---|---|---|
| 2,935,068 | 5/1960 | Donaldson | 128/348 |
| 3,505,991 | 4/1970 | Hellerstein et al. | 128/1.1 |
| 3,663,965 | 5/1972 | Lee et al. | 128/348 X |
| 3,765,032 | 10/1973 | Palma | 128/348 X |
| 3,783,868 | 1/1974 | Bokros | 128/348 X |
| 3,815,577 | 6/1974 | Bucalo | 128/1 R |
| 3,998,222 | 12/1976 | Shihata | 128/214 R |
| 4,015,601 | 4/1977 | Bokros et al. | 128/214 R |

*Primary Examiner*—Dalton L. Truluck

*Attorney, Agent, or Firm*—Fitch, Even, Tabin & Luedeka

[57] ABSTRACT

A device to provide access to the circulatory system of a living body includes at least one tubular conduit and a housing integrally associated with the conduit and having fluid communication therewith through an aperture in the conduit wall at the point where the wall intersects the housing. Inside the housing is a rotatable valve adapted to receive a catheter to extend the fluid communication outside the living body. The valve is rotatable in the housing to selectively establish fluid communication between the circulatory system and the outside of the living body by means of a cannula receptacle provided in engaging relation with the valve. The cannula receptacle is adapted to engagingly receive the catheter. Structural restrictions, however, allow insertion and withdrawal of the catheter only when the valve is closed. Rotation of the valve occurs through the rotation of the catheter when the catheter is engagingly inserted in the cannular receptacle. A cap having a central aperture and a circumferential slot on its inner wall is provided to cover the open end of the assembly and to assure continuous seating of the valve. A tab is provided on the catheter tip to engage the circumferential slot and interlock the system when the valve is open.

5 Claims, 14 Drawing Figures

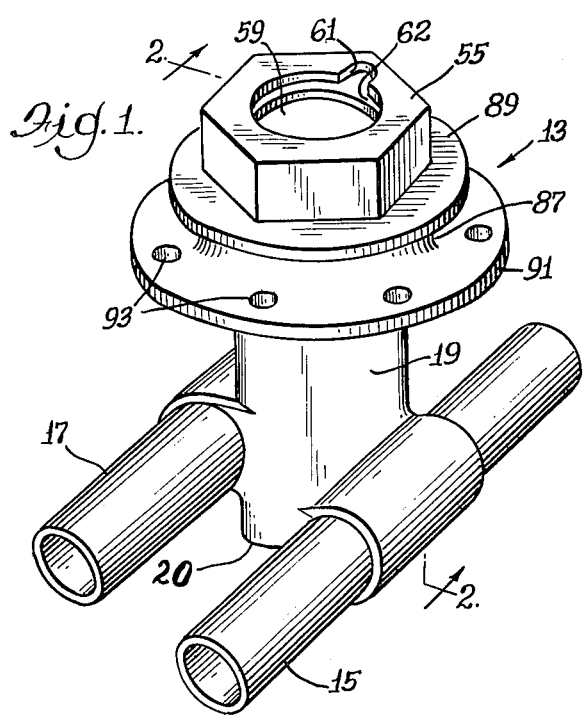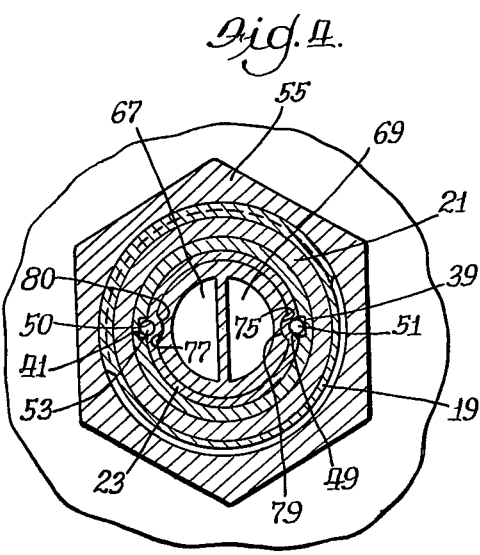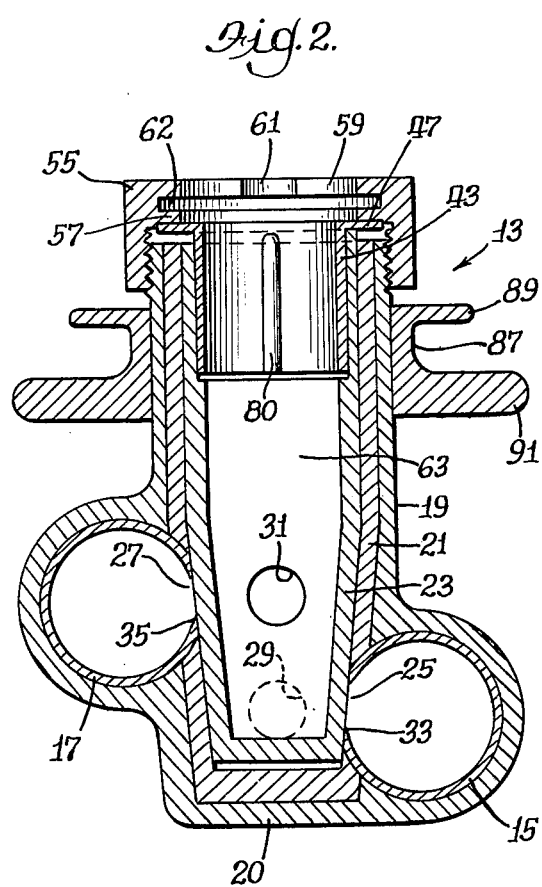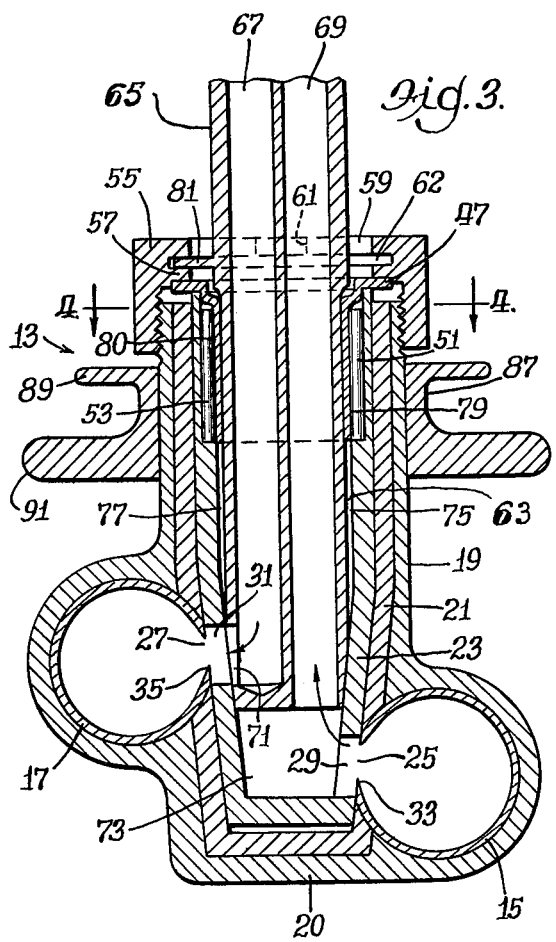

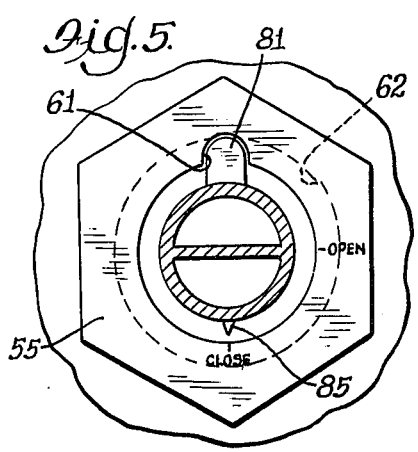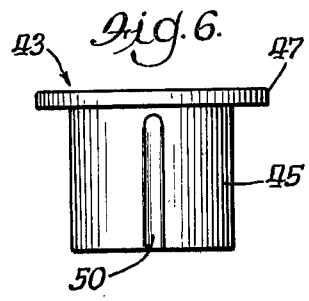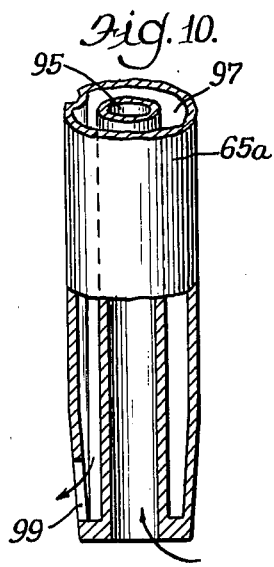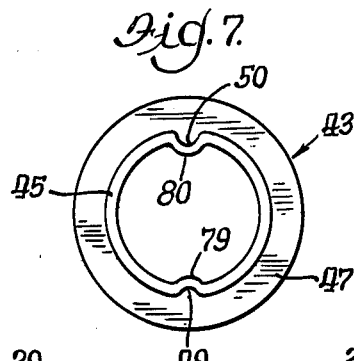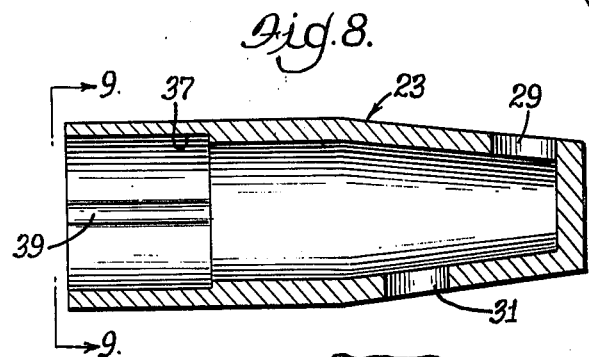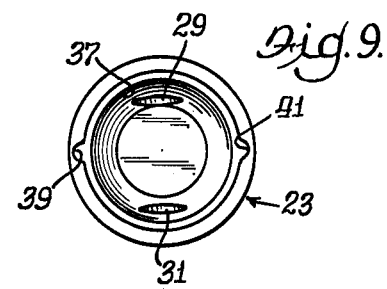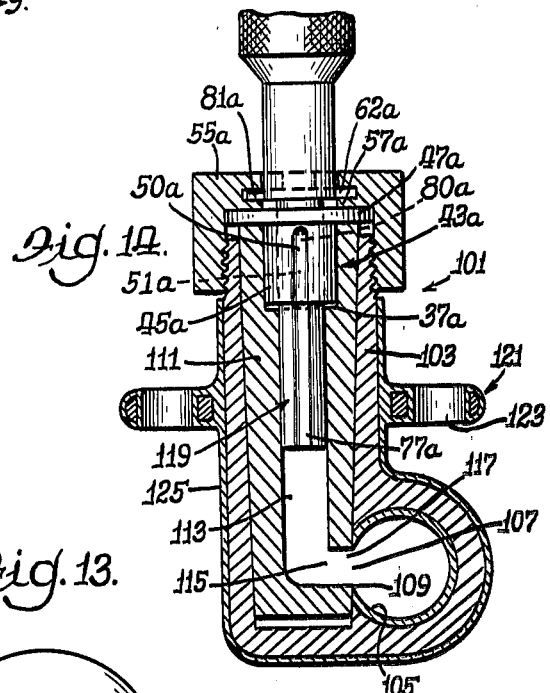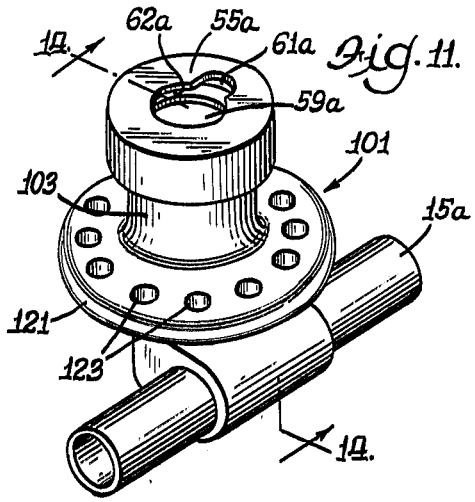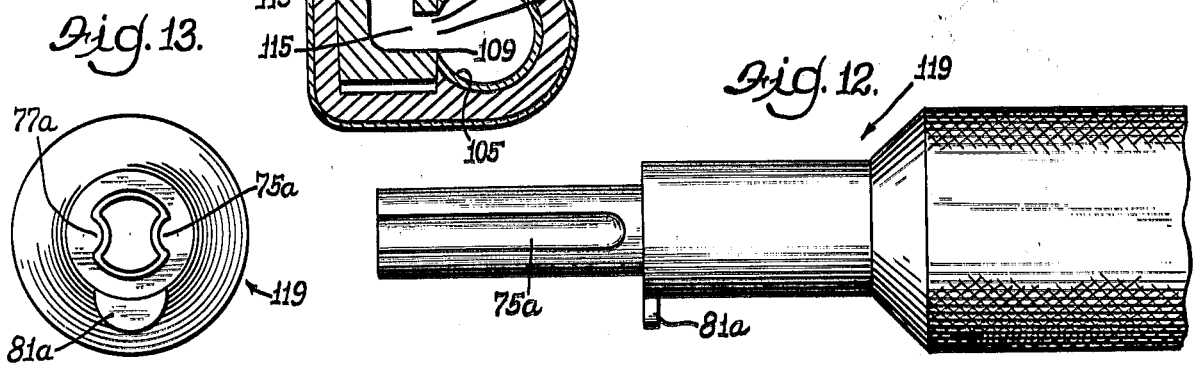

CATHETER INTERLOCK SYSTEM

This is a continuation-in-part of application Ser. No. 764,207, filed Jan. 31, 1977.

This invention relates to medical devices and, more particularly, to an improvement in devices that provide access to the circulatory system of a living body.

There is a need in devices that provide access to the circulatory system of a living body, for example, to tap the blood supply for passing the blood externally of the body through a blood dialyzer. An individual could require the use of a dialyzer over an extended period of time, and it is desirable for devices to be available for implanting in the body for immediate connection of catheters to the circulatory system at any desired time. As implants, however, such devices should be biologically compatible with the living tissues surrounding them. In this connection, the devices should not prevent healing, irritate tissues, or stimulate a prolonged rejection response by the living body. Further, the devices should be physiologically inert over prolonged periods of time and should be mechanically strong and reliable. It is desirable that such devices in combination with at least the tips of the catheters provide positive, error-free access to the blood.

In copending application Ser. No. 622,090, filed Oct. 14, 1975 now U.S. Pat. No. 4,015,601, issued Apr. 5, 1977,, and assigned to the assignee of this invention, an access device is described which provides means for forming fluid communication between the outside and the circulatory system. Such a device is uni-directional, i.e., allows fluid passage in one direction at a time. Described herein is a device that is duo-directional, i.e., provides access to the circulatory system for simultaneous withdrawal and return of blood to the system.

Although skilled and trained personnel, such as doctors, nurses, and medical technicians, work with such blood access devices, it is desirable that the possibility for human error in connecting and disconnecting the catheters to the implanted blood access devices be minimized.

Accordingly, it is an object of this invention to provide a system for joining catheters to implanted blood access devices that will permit positive engagement and disengagement of the joined parts while maintaining the valves of the devices in their seated conditions.

It is another object of this invention to provide a system of the foregoing type whereby the valves are rotated by rotation of the catheters after such positive engagement between the parts has been established.

It is a further object of this invention to provide a system of the foregoing type whereby removal or disengagement of the catheters from the joined condition of the implanted access devices is prevented when the valves of the devices are open.

The accomplishment of these and other objects of the invention will become apparent from the following description and its accompanying drawings of which:

FIG. 1 is a perspective view of a duo-directional blood access device embodying various features of the invention and adapted for implantation in a living body;

FIG. 2 is a vertical sectional view of the device of FIG. 1 taken along the line 2—2 and illustrating parts nonaligned (valve closed) to prevent fluid communication between parts;

FIG. 3 is a view similar to FIG. 2, but illustrating parts aligned (valve open) for fluid communication and illustrating one form of a catheter inserted in the device to extend the communication externally of the body and also illustrating structural features of the system that prevent removal of the catheter when the valve is open;

FIG. 4 is a cross-sectional view of the device taken along line 4—4 of FIG. 3;

FIG. 5 is an end view of the device with part in section;

FIG. 6 is a side view of a catheter receiving member of the device;

FIG. 7 is an end view of the member of FIG. 6;

FIG. 8 is a sectional view of a valve member of the device;

FIG. 9 is an end view of the device taken along the line 9—9 of FIG. 8;

FIG. 10 is an alternative construction of a catheter tip suitable for insertion in the device of FIG. 3;

FIG. 11 is a perspective view of a uni-directional blood access device also embodying various features of the invention and adapted for implantation in a living body;

FIG. 12 is a catheter tip embodying features of the invention for insertion in the device of FIG. 11;

FIG. 13 is an end view of the catheter tip of FIG. 12; and

FIG. 14 is a vertical sectional view of the device of FIG. 11 taken along the line 14—14 and illustrating structural features that prevent the removal of the catheter tip when the valve of the device of FIG. 11 is open.

The features that provide a system for joining catheters to implanted blood access devices in accordance with the invention are first described in connection with a duo-directional blood access device for implantation in a living body. Such duo-directional access device of the invention includes three principal outer portions, two of which are generally parallel to one another and the other of which is generally at right angles to the two parallel portions. Both parallel portions are tubes having open ends. Either one may be inserted longitudinally in a blood vessel, the other being available for connection to a bypass in the form of a graft either upstream or downstream of the same blood vessel. The third major portion is a housing with one end open and the other closed, the housing containing a valve for establishing fluid communication with the blood in the blood vessel. The valve is adapted to receive a dual-conductor catheter which is used to establish a blood flow line simultaneously in and out of the circulatory system. The device is structured of materials that are biologically compatible with the blood and tissues of a living body in which it is inserted. At least all blood contacting surfaces are carbon. Further, the material is physiologically inert over prolonged periods of time and is mechanically strong and reliable, all of which is described in detail hereinafter.

Referring now to FIG. 1, there is shown a blood access device 13 having a pair of parallel conduits 15 and 17 and a housing 19 having a closed end 20, the conduits being adjoined near the closed end. In this illustrated embodiment, both the conduits 15 and 17 are round tubular open-ended structures, and the housing 19 is generally cylindrical in form. The conduits 15 and 17 are generally parallel to one another and are generally at right angles to the axis of the housing 19.

In FIG. 2 it will be seen that several members are mounted internally of the housing 19. Immediately inside the walls of the housing 19 is a liner 21, and immediately inside the liner 21 is a valve body 23. It will be noted that the housing 19 is generally cylindrical with the inner portion of the housing being tapered toward its closed end. Both the liner 21 and valve body 23 are generally cylindrical, each having a closed end and an open end. They both taper inwardly toward their closed ends, the respective tapers conforming to that of the housing interior. The liner 21 forms a snug or close-fitting relation with the internal portion of the housing 19, as does the valve body 23 within the liner 21. Nonetheless, the valve body is coaxially rotatable within the liner 21 and housing 19, the liner being fixed to the housing interior by a suitable epoxy or cement. The liner 21 is dimensioned so that it will completely line the interior wall of the housing 19 and fit against the closed end of the housing. It is important that the valve body 23 form a tight seal with the liner 21, and for this reason, the closed end of the valve body 23 does not bottom on the interior end of the liner 21. Clearance is provided to assure adequate seating of the valve body within the liner along the tapered interface to form, as will be described in detail hereinafter, a liquid and bacterial seal. Some very slight differences in diameters of the respective parts can be tolerated with this tapered structure. Preferably, both the valve body 23 and the liner 21 are made of pyrolytic carbon and the housing 19 is made of titanium, as fully described hereinafter.

FIG. 2 shows the device 13 with the valve body 23 in the closed position, i.e., there is no fluid communication between the interiors of both the conduits 15 and 17 and the interior of the valve body 23. To provide such fluid communication between these interiors, the conduits 15 and 17 are provided with apertures 25 and 27 respectively through the conduit walls. Although the conduits 15 and 17 are generally parallel to each other, their points of adjoining the housing are displaced from each other with respect to the axis of the housing 19, as well as being spaced away from the axis itself. Accordingly, the apertures 25 and 27 are spaced apart from each other axially of the housing 19, and to complete the fluid communication to the interior of the valve body 23, there are provided ports 29 and 31 in the wall of the valve body located to be alignable with the apertures 25 and 27 at a given rotative position of the valve body 23. Referring briefly to FIG. 3, such alignment is seen. Because of the axial displacement of these apertures and their corresponding ports, there is only one rotative position of the valve body in which fluid communication will be established between the interiors. Referring once again to FIG. 2, the valve body is shown with a 90° rotation from the position of alignment, but even at a 180° rotation from the position of alignment, it will be seen that fluid communication will not be established. The apertures 25 and 27 are each defined by a perimeter formed of a sharp edge 33 and 35 respectively of the conduit walls.

The valve body 23 with its ports 29 and 31 is shown separately in FIG. 8. There it will be seen that a counterbore 37 is provided in the open end of the body. FIG. 9 is a view looking into the open end of the valve body 23, and it will be seen that a pair of grooves 39 and 41 are provided in the inner surface of the counterbore 37. These grooves are coterminous with the counterbore and extend in a direction axially of the valve body.

The purpose of the counterbore 37 is to receive and hold a cannula receptacle 43 shown in FIGS. 6 and 7. This receptacle includes a cylindrical body 45 and a top flange 47. The body 45 has an outside diameter that forms a snug fit when the receptacle is inserted in the counterbore 37 at the open end of the valve body 23.

A suitable epoxy or other cement is used to affix the cannula receptacle 43 to the valve body 23 after the desired rotative position of the receptacle with respect to the valve body has been established. This desired position involves a pair of grooves 49 and 50 in the outer surface of the body wall 45 extending in a direction axially of the cannula receptacle. The grooves 49 and 50 are in the outer surface of the body wall and are semicircular in cross section. The grooves 39 and 41 are in the inner surface of the counterbore 37 are semicircular in cross section and are substantially of the same diameter as the grooves 49 and 50. When the receptacle 43 is inserted in the counterbore 37, the receptacle is rotated until the grooves in the receptacle oppose the grooves in the counterbore, thus forming two cylindrical openings at these locations extending in a direction axially of the combined cannula receptacle 43 and valve body 23.

Referring now to FIGS. 3 and 4, a pair of rods 51 and 53, preferably of stainless steel, are inserted in the cylindrical openings formed by the opposing grooves, the suitable epoxy first having been applied to the interface between the cannula body wall 45 and the valve body counterbore 37. The relationship between the receptacle 43 and the valve body 23 then becomes fixed. As will be seen hereinafter, the cannula receptacle 43 is instrumental in causing the rotation of the valve body 23 between positions of alignment and nonalignment of the apertures and ports to selectively establish fluid communication therethrough, and the stainless steel rods form an interlock in the opposing grooves as a safety feature in the event the epoxy should for any reason let loose. The rods thus assure unison rotative movement between the cannula receptacle and the valve body whenever rotative force is applied to the cannula receptacle, which occurs with the aid of a catheter as described hereinafter.

A cap 55 is applied over the open end of the housing 19, the liner 21, and the valve body 23, including the affixed cannula receptacle 43. The cap 55 is of a screw type, and the outer surface of the housing 19 near its open end is threaded to accommodate the cap 55. A shoulder 57 on the interior of the cap 55 bears down upon the flange 47 of the cannula receptacle to securely retain the valve body 23 affixed to the receptacle in a seated position within the liner and housing.

As best seen in FIG. 1, the cap 55 is provided with a generally circular orifice 59 having a key slot 61 extending outwardly from a point along its general circumference. The key slot serves as an entrance to a circumferential slot 62 formed in the inner wall of the cap 55, the purpose of which is described hereinafter. A generally longitudinal passage 63 (FIG. 2) begins at the orifice 59 and extends through the cannula receptacle 43 to the closed end of the valve body 23.

Referring now to FIG. 3, this longitudinal passage 63 receives a catheter 65 inserted to establish a flow path for the blood when blood passage is established by alignment of the ports 29 and 31 with the apertures 25 and 27 respectively in accordance with the invention. The catheter 65 is tapered on its end outer surface to conform to the interior taper of the longitudinal passage 63 in the interior closed end portion of the valve body 23. To effect simultaneous withdrawal and return of blood from the living body, the catheter 65 is of dual-conduit design, having a pair of side-by-side conduits 67 and 69. The conduit 67 is closed at the tip of the catheter, and fluid communication to the port 31 of the valve body 23 is established through a side port 71 of the catheter wall positioned to align with the port 31 when the catheter tip is completely inserted. The conduit 69, on the other hand, is open-ended and provides immediate fluid communication with a cavity 73 at the closed end of the valve body 23 between the tip of the catheter and the inside end of the valve body. The port 29 is, of course, in communication with the cavity 73, and a fluid flow is thus established from the interior of the conduit 15 to the conduit 69 when the port 29 is aligned with the aperture 25 in the wall of the conduit 15.

Although arrows in FIG. 3 indicate a directional flow from the interior of the conduit 15 outwardly through the conduit 69 and return through the conduit 67 to the interior of the conduit 17, it should be understood that this is for the purpose of depicting a simultaneous outward and return flow of a fluid in the blood access device 13, rather than for stressing a particular direction of flow. The direction of both arrows could be reversed to indicate a reverse direction of flow in accordance with the invention.

The catheter 65 is inserted into the longitudinal passage 63 when the valve is closed, i.e., when the ports 29 and 31 are in a nonaligned relation with the apertures 25 and 27 respectively. To establish a passage for blood in accordance with the invention, the catheter 65 is used as an instrument to rotate the valve body 23 to align the ports with the apertures. After such rotation, the valve is open and a passage for blood is established.

To effect such rotation of the valve body by the catheter 65, the catheter tip is further provided with a pair of flutes 75 and 77 in the outer walls of the catheter tip that are located 180° from each other, and a pair of longitudinal guides 79 and 80 (FIG. 7) are located on the back sides respectively of grooves 49 and 50 in the body wall 45 of the cannula receptacle 43. Accordingly, before the catheter 65 can be inserted in the longitudinal passage 63, the catheter must be rotated to align the flutes 75 and 77 with, and thus engage, the longitudinal guides 79 and 80 upon insertion of the catheter. Because the cannula receptacle which the catheter thus engages is affixed to the valve body 23, the valve body will be rotated upon rotation of the catheter.

It would be completely undesirable for the catheter 65 to be removable when the valve is open and blood is flowing. To avoid such a circumstance, a lug 81 extending at right angles outwardly from the catheter wall is provided on the catheter 65. As best seen in FIG. 5, this lug is shaped and sized to pass freely through the key slot 61 in the cap 55, when the valve is closed and the catheter is aligned for insertion therein. The circumferential slot 62 provided in the cap 55 receives the lug 81 and retains the catheter 65 in its seated position when the catheter is rotated to open the valve. Thus, it may be seen in FIG. 1 that the insertion of the catheter 65 will stop after the lug 81 has entered and passed through the key slot 61. Rotative movement to open the valve thereafter occurs.

Referring once again to FIG. 5, the cap 55 is also provided with indicia to indicate the particular relative rotative positions of the catheter 65 and the cap 55. A small protrusion 85 in the form of a pointer is provided on the catheter at a position 180° from the lug 81 and a mark with the word "open" or the like is provided on the top surface of the cap at a point to which the catheter 65 must be rotated to effect the opening of the valve. Because the lug 81 at that point is secure in the slot 62, the catheter can only be removed when the valve is closed by a rotation of the catheter adequate to align the lug 81 with the key slot 61 for removal. Thus, to interrupt the blood passage, the catheter 65 is rotated at least one-quarter of a turn, and at this point the ports and the apertures are not aligned. Because of the close-fitting, seated relation of the valve body 23 with the liner 21, there is a liquid and bacterial seal established around the sharp edges 33 and 35 respectively of the apertures 25 and 27, as is more completely described hereinafter. The bacterial seal is a barrier to the invasion of bacteria in the blood stream through the interfaces of the moving parts of the blood access device 13.

Returning to FIG. 1, around the perimeter of the housing 19 is a stabilizing button 87 that has the appearance in a sectional view (e.g., FIGS. 2 and 3) of a collar button, a smaller flange 89 being at one end of the button and a larger flange 91 being at the other end. In practice, this button is applied over the housing such that the smaller flange 89 will be disposed at the approximate level of the skin surface. These flanges on the button project outwardly from the housing, and the larger flange 91 carries a plurality of holes 93. When the blood access device 13 is implanted in a human body, body tissue will grow in and around the holes 93 and stabilize the position of the blood access device in the body. The position of the button 87 may be movable axially of the housing to control the extent the housing extends beyond the surface of the skin, or the position of the button may be fixed if uniformity of housing height above the flange is found to be desirable. Further, it may be desirable to also include an epithelium stopping means in the form of another collar (not shown) between the flanges 89 and 91, as described in U.S. Pat. No. 3,783,868, issued Jan. 8, 1974, to inhibit the progressive growth of epithelium tissue down and around the housing 19.

It should be recognized that although the blood access device 13 is useful in a living human body, it may also have veterinary or scientific applications in living animals, domestic or wild. It should also be understood that the device of the invention may be inserted in any part of a circulatory system as needed.

The device 13 is inserted in the living body by any suitable surgical procedure. Generally, a longitudinal incision is made through the skin at the desired location for insertion in the blood vessel, and an incision is made in the blood vessel after momentarily stopping the flow of blood therethrough. Sutures (not shown) are then used to sew up the blood vessel after the ends of the conduit 15 have been inserted therein, and other sutures (not shown) are used to sew up the skin around the housing 19 as illustrated. In this connection, it is noted that the length of the housing 19 above the point of association with the conduit 15 is sufficient to extend from the blood vessel in which the conduit 15 is inserted to a point outside the living body, i.e., outside the skin layer. Alternatively, the blood vessel may be severed and the severed ends slipped over the protruding ends of the conduit 15 without engaging the device housing 19. The conduit 17 is then connected to the circulatory system by a graft at points upstream or downstream from the incision and insertion of the conduit 15. Although for purposes of description, the conduit 15 has been described and illustrated as being inserted in the blood vessel, and the conduit 17 as being connected to the graft, it is in accordance with the invention that the conduit 17 could be inserted in the blood vessel and conduit 15 connected to the graft, at the option of the surgeon.

An alternative construction of a dual-conduit catheter is illustrated in FIG. 10 by catheter 65a. Here the two conduits are arranged concentrically rather than side-by-side while the external construction is fluted and tapered the same as the catheter 65 described previously. Thus, a conduit 95 is open-ended and forms the center conduit, and a conduit 97 is concentric with the conduit 95, but is closed-ended and has as its opening a port 99 in its side wall. Referring briefly again to FIG. 3, it will be seen that this alternative catheter 65a may be inserted in the same manner as the catheter 65, it being understood that the alternative catheter 65a will have a pair of flutes and a lug the same as the flutes 75 and 77 and lug 81 of the catheter 65. It should be understood also that when the alternative catheter 65a is inserted in the blood access device 13, the port 99 will align with the port 31 in the valve body 23, and so the conduit 97 will have fluid communication with the interior of the conduit 17, whereas the conduit 95 will have fluid communication through the cavity 73 to the interior of the conduit 15.

As mentioned previously, because the blood access device 13 is inserted within a living body, it is important that the material of the device be biocompatible (biologically compatible) with the blood and living tissues which surround it. Furthermore, the device, once inserted, should not prevent healing, irritate tissues, or stimulate a strong or prolonged rejection response by the living body, and the material of the device should be physiologically inert over long periods of time in addition to being mechanically strong and reliable.

In accordance with the invention, a coating of carbon is utilized on all blood contacting surfaces and on the housing/skin interface. This carbon coating may be pyrolytic carbon, vapor-deposited carbon or vitreous carbon, and these kinds of coatings may be utilized on different parts of the blood access device 13. Pyrolytic carbon, vitreous (glassy) carbon, and vapor-deposited carbon are compatible with the surrounding tissues over prolonged time periods when inserted through the skin layer of a living body. Preferably, pyrolytic carbon and/or vapor-deposited carbon are used. These coatings do not tend to irritate the surrounding skin tissues and they promote the establishment of a barrier to external pathogens.

In general, the preferred construction of the device 13 includes a metallic housing, such as titanium, stainless steel or a chromium-cobalt alloy such as VITALLIUM. Preferably, the housing is constructed of titanium. The conduits 15 and 17 are constructed of pyrolytic carbon and may be formed in any suitable manner, such as deposition of a built-up coating on a mandrel, after which the mandrel is removed, leaving the tube-like structures. Both the liner 21 and the valve body 23 are constructed by preshaping a suitable substrate, such as a graphite core, in the general form of a cylinder and having one end taper gradually to a reduced diameter. A coating of the pyrolytic carbon is then made thereon, and the graphite is removed, as by drilling, leaving a pyrolytic carbon shell. The interfacial surfaces, particularly of the tapered portions, are lapped and polished to enhance a close-fit relation with adjacent parts. The ports are then made in a suitable manner, as by drilling. The button 87 also is constructed on a suitable substrate or graphite core which is preshaped to the desired form, which includes both the smaller flange 89 and the larger flange 91, the holes 93 then being formed in the flange 91, such as by drilling, and a pyrolytic carbon coating being applied to the core, including the inner surfaces of the holes 93. Preferably, on this button the carbon coating has a rough finish. The core materials and the process of applying the pyrolytic carbon coatings are described in detail hereinafter.

The cannula receptacle 43 preferably is made from stainless steel and formed in a suitable manner, such as by a stamping and drawing operation. The cap 55 is machined in a suitable manner, preferably from stainless steel, as are also the interlocking rods 51 and 53 (FIG. 4).

One such blood access device 13 has been constructed in which the overall length of the housing 19 is approximately 0.8 inch and its outer diameter is approximately 0.35 inch. The location of the conduit 17 with respect to the open end of the housing 19 is such that the axis of the conduit 17 is approximately 0.5 inch from the open end. The overall diameter of the larger flange 91 is approximately 0.75 inch. The holes 93 in the flange 91 are 0.1 inch in diameter. The pyrolytic carbon wall thickness of both the liner 21 and the valve body 23 is approximately 0.03 inch. The diameter of the longitudinal passage 63 inside the valve body 23 is 0.19 inch, and from such diameter the walls taper inwardly at an angle of 5° 45'. The interlocking stainless steel rods 51 and 53 are 0.01 inch in diameter and are approximately 0.2 inch long.

These dimensions are provided by way of giving an example of construction, but there is no intention of requiring the construction to be limited to any of these dimensions.

As seen in FIGS. 2 and 3, when the conduits 15 and 17 are inserted and joined to the housing 19, the side walls of the conduits intersect the liner 21 and valve body 23. The portion of the conduit wall that would intersect the valve body 23 is formed in a suitable manner, as by grinding, to conform to the general shape of the circular outer surface of the valve body 23 to form a seat for the valve. The interfacial surfaces are then lapped and polished to form a good seal therebetween in this snug or close-fitting relation. In this connection, a very important step in making the blood access device 13 is the lapping of the portion of the external surface of the conduits 15 and 17 that are in contact with the valve body 23 to conform these portions to the circular surface of the valve body so as to produce the sharp edges 33 and 35 (FIGS. 2 and 3) as well as seats for the valve. Such a sharp edge does not permit the accumulation and coagulation of blood around the aperture. Thus, after having once established fluid communication between a blood vessel and the catheter 65 or 65A and then closing the valve body by rotation thereof, the blood flow will be cleanly interrupted with no places for accumulation or coagulation of the blood in the conduits 15 and 17. After the valve is closed, any residual blood in the valve body 23 may be flushed out by using a suitable cleansing solution. Thereafter, a suitable plug (not shown) may be applied over the end of the cap 55 to keep the interior clean until next use.

The pyrolytic carbon may be deposited upon the mandrels in the instance of the conduits 15 and 17 and upon the core materials for the other parts in the manner described in U.S. Pat. No. 3,783,868 and U.S. Pat. No. 3,298,921. An example of a coating method that may be employed is that of supporting the formed substrate on a rotating or stationary mandrel within a large fluidized bed, as discussed in the aforementioned patents, or coating on freely moving rods in a fluid bed.

Pyrolytic carbon is, by definition, deposited by the pyrolysis of a carbon-containing substance. Accordingly, the core material on which the pyrolytic carbon is deposited will be subject to the fairly high temperatures necessary for pyrolysis. Generally, hydrocarbons are employed as the carbon-containing substance to be pyrolyzed, and temperatures of at least about 1000° C are used. Some examples of deposition of pyrolytic carbon are set forth in the aforementioned U.S. Pat. No. 3,298,921. Processes illustrated and described in this patent employ methane as the source of carbon and utilize temperatures generally in the range of about 1200° C to 2300° C. Although it is possible to deposit pyrolytic carbon having the desired properties with regard to this invention at somewhat lower temperatures by using other hydrocarbons, for example, propane or butane, it is generally considered that the core material should remain substantially stable at temperatures of at least about 1000° C and preferably at even higher temperatures. Pyrolytic carbons deposited at temperatures below about 1500° C are particularly suited for use in the blood access device 13, because such pyrolytic carbons have exceptional tissue compatibility and mechanical reliability.

Examples of core materials which have the aforementioned stability at high temperatures include artificial graphite, boron carbide, silicon carbide, refractory metals (and alloys), such as tantalum, titanium, molybdenum, tungsten, and various ceramics, such as mullite. A preferred substrate material is polycrystalline graphite. An example of such a graphite is the polycrystalline graphite sold under the trademark POCO.

Vapor-deposited carbon coatings may be applied by the process described in U.S. Pat. No. 3,952,334 "Biocompatible Carbon Prosthetic Devices", issued Apr. 27, 1976. As generally described therein, a substrate is placed in an evaporative coater and a vacuum is established. A crucible within the coater, filled with a commercial grade of artificial graphite, is heated by electron beam bombardment. Coating is carried out until the desired thickness of carbon is deposited and the substrate is then removed. This process results in an exterior carbon layer that is smooth and uniform.

The features that provide a system for joining catheters to implanted blood access devices in accordance with the invention are next described in connection with a uni-directional blood access device. Such uni-directional access device, i.e., a device in which the fluid flows in only one direction at a time, is shown in FIGS. 11 and 14 as device 101. Reference numbers with subscript "a" are used to indicate parts in this device 101 that are like corresponding parts of the device 13 described earlier. A conduit 15a is a round tubular structure, open-ended, and intended for insertion in a blood vessel in the same manner as either the conduits 15 or 17 of the device 13 (FIG. 1). This conduit 15a adjoins a housing 103 along the side wall of the housing. The interiors of the two parts are separated by a wall 105 common to both. In the common wall is an aperture 107 that provides fluid communication between the two interiors and is defined by a perimeter formed by a sharp edge 109 of the common wall.

In the housing 103 is a valve body 111. At least the interior surface of the housing 103 is tapered as indicated and at least the outer surface of the valve body 111 is tapered in a conforming manner to the housing interior. These conforming tapered surfaces afford a very close interfitting relationship. Nonetheless, the valve body 111 is movable within the housing. Specifically, in this illustrated device 101, the valve body and the housing are coaxially related, and the valve body is rotatable about the axis in the housing.

Facilitating this rotation is a cannula receptacle 43a inserted in an affixed relation in a counterbore 37a provided in the open end of the valve body 111. Similar to those shown in FIG. 9, grooves 39a and 41a are provided in the inner surface of the counterbore 37a. These grooves also are coterminous with the counterbore and extend in a direction axially of the valve body.

The cannula receptacle 43a also is provided with a body 45a and a top flange 47a. The body 45a has an outside diameter that forms a snug fit when the cannula receptacle is inserted in the counterbore. A suitable epoxy or other cement is used to affix the cannula receptacle 43a to the valve body 111 after the desired rotative position of the receptacle with respect to the valve body has been established. This desired position involves the pair of grooves 49a and 50a (corresponding to grooves 49 and 50 in FIG. 7) in the outer surface of the body wall 45a extending in a direction axially of the cannula receptacle. These grooves 49a and 50a are 180° apart in the outer surface of the body wall and are semi-circular in cross section as are the grooves 39a and 41a, also 180° apart, in the inner surface of the counterbore 37a of the valve body 111. When the cannula receptacle 43a is inserted in the counterbore 37a, the receptacle is rotated until the grooves in the receptacle oppose the grooves in the counterbore, thus forming two cylindrical openings at these locations extending in a direction axially of the combined cannula receptacle 43a and valve body 111 in a manner similar to that shown in FIG. 4. A pair of rods 51a and 53a, preferably of stainless steel, are inserted one for one in the cylindrical openings formed by the opposing grooves, a suitable epoxy having first been applied to the interface between the cannula body wall 45a and the valve body counterbore 37a. The relationship between the receptacle 43a and the valve body 111 then becomes fixed. The stainless steel rods form an interlock in the opposing grooves as a safety feature in the event the epoxy should for any reason let loose. The rods thus assure unison rotative movement between the cannula receptacle and the valve body whenever rotative force is applied to the cannula receptacle, which occurs with the aid of a catheter described hereinafter.

The valve body 111 is generally in the form of a pyrolytic carbon cylinder having a lower closed end and a longitudinal passage 113 parallel to the common axis and a transverse passage 115 at an angle thereto terminating in a port 117. The longitudinal passage 113 is located coaxially of the housing 103. The transverse passage 115 is located so as to align the port 117 with the aperture 107 in a given axially rotative position of the valve body 111 to establish fluid communication between the conduit 15a and the interior of the valve 111 in the housing 103. The longitudinal passage 113 receives a catheter tip 119 in completing a flow path for the blood. Blood flow is established by aligning the port and the aperture in accordance with the invention.

The catheter is inserted in the longitudinal passage 113 when the valve is closed, i.e., the port 117 is in a non-aligned relation with the aperture 107. To establish a passage for blood in accordance with the invention, the catheter tip 119 is used as an instrument to rotate the valve body 111 to align the port with the aperture. After such rotation, the valve is open and a passage for blood is established.

To effect such rotation of the valve body by the catheter tip 119, the catheter tip is provided with a pair of flutes 75a and 77a in its outer walls. These flutes are located 180° from each other, and a pair of longitudinal guides 79a and 80a (similar to 79 and 80 in FIG. 7) are located on the back sides respectively of the grooves 49a and 50a. Accordingly, before the catheter tip 119 can be inserted in the longitudinal passage 113, the catheter must be rotated to align the flutes 75a and 77a with, and thus engage, the longitudinal guides 79a and 80a upon insertion of the catheter. Because the cannula receptacle which the catheter thus engages is affixed to the valve body 111, the valve body will be rotated upon rotation of the catheter.

As mentioned in connection with the description of the device 13 of FIG. 1, it would be completely undesirable for the catheter tip 119 to be removable when the valve is open and blood is flowing. To avoid such a circumstance, a lug 81a extending at right angles outwardly from the catheter tip wall is provided on the catheter tip 119. As seen in FIGS. 12 and 13, this lug is semicircular in shape when viewing from the end and flat when viewing from the side.

It will be noted that the lug 81a is circumferentially displaced 90° from the flutes in the illustrated catheter tip 119 of FIG. 12, whereas the lug 81 is aligned with one of the flutes as illustrated in the device of FIG. 3. The circumferential position of the lug will depend on the interrelationship between the valve body, cannula receptacle, catheter tip and cap. It is of importance that this interrelationship establish the conditions in which the catheter can be inserted and removed only when the valve is closed and the catheter is locked in the inserted position when the valve is open. The circumferential position of the lug, then, must be in conformity with the relationship of the other ports that establish these conditions.

A cap 55a is applied over the open end of the housing 103 and the valve body 111, including the affixed cannula receptacle 43a. The cap 55a is of a screw type, and the outer surface of the housing 103 near its open end is threaded to accommodate this cap 55a. A shoulder 57a on the interior of the cap 55a bears down upon the flange 47a of the cannula receptacle to securely retain the valve body 111 affixed to the receptacle in a rotatively seated position within the housing.

As best seen in FIG. 11, the cap 55a is provided with a generally circular orifice 59a having a key slot 61a extending outwardly from a point along its general circumference. The key slot serves as an entrance to a circumferential slot 62a formed in the inner wall of the cap 55a. The circumferential slot 62a receives the lug 81a and retains the catheter tip 119 in its seated position after the catheter is rotated to open the valve. Thus, it may be seen in FIG. 11 that the insertion of the catheter tip 119 will stop after the lug 81a has entered and passed through the key slot 61a. Rotative movement to open the valve thereafter occurs. The interlocking relation thus established between these parts prevents an inadvertent removal of the catheter 119 when the valve is open and blood is flowing. When the valve is open, fluid may flow in either direction, one direction at a time, in the established passage as circumstances direct.

The cap 55a may also be provided with indicia to indicate the particular relative rotative position of the catheter 119 and the cap 55a similarly as shown in FIG. 5. Thus, a small protrusion in the form of a pointer may be provided on the catheter at a position 180° from the lug 81a, and a mark with the word "open" or the like may be provided also on the top surface of the cap at a point to which the catheter 119 must be rotated to effect the opening of the valve. Because the lug 81a at that point is secure in the slot 62a, the catheter can only be removed when the valve is closed by a rotation of the catheter adequate to align the lug 81a with the key slot 61a for removal. To interrupt the blood passage, the catheter 119 is rotated at least one-quarter of a turn, as indicated, or even a full one-half turn (not shown) to assure that the port and aperture are not aligned.

When the aperture and the port are not aligned, i.e., the valve is closed, a portion of the outer surface of the tapered side wall of the valve body 111 completely covers the aperture 107 and establishes a liquid and bacterial seal therearound. To facilitate this seal, the valve body extends below the aperture to provide additional surface in close-fitting relation with the interior of the housing 103. The narrow end of the valve body does not bottom on the inside of the housing, and there is clearance to assure adequate seating of the valve body within the housing along the tapered interface to form the liquid and bacterial seal. Some slight differences in diameters of the respective parts can be tolerated with this tapered structure. For hygienic purposes, the interior of the valve should be flushed out with a suitable cleansing solution on a regular basis.

A stabilizing flange 121 having holes 123 may be provided around the perimeter of the housing 103 in a manner similar to that described in connection with the button 87 on the device 13 (FIG. 1). The body tissue grows in and around the holes 123 to stabilize the position of the device 101 in its implanted condition. This flange may be affixed on the outside of the housing in a desired axial position by a suitable epoxy or cement.

In general, the device 101 is constructed in a manner similar to that already described in connection with the device 13, i.e., the housing machined from a metal, preferably titanium, and the conduit 15a being pyrolytic carbon and prepared on a mandrel. In this instance, the valve body 111, however, may be prepared on a graphite core with a pyrolytic carbon coating applied on the surfaces of the core. The graphite is then removed, as by drilling, leaving a pyrolytic carbon shell as the valve body. The interfacial surfaces of the tapered portions are lapped and polished to enhance the close-fit relation with the housing. The housing 103 may also be coated on its exterior surface with a layer 125 of pyrolytic carbon.

An important step in constructing this device 101, is the lapping of the outer surface of the portion of the conduit wall 15a adjacent the lower end of the valve body 111 in the housing 103 to provide the sharp edge 109 that defines the aperture 107. As described previously in connection with the device 13, such a sharp edge does not allow the accumulation and coagulation of blood around the aperture. Thus, after having once established fluid communication between a blood vessel and the catheter 119 and then closing the valve by rotating the valve body 111, the blood flow will be cleanly interrupted with no places for accumulation or coagulation of the blood in the conduit 15a. When the valve is closed and the catheter removed, any residual blood in the longitudinal passage 113 and the transverse passage 115 is flushed out by using a suitable cleansing solution. Thereafter, a suitable plug (not shown) may be inserted in the upper end of the longitudinal passage to keep the interior clean until next use.

Summarizing, there has been shown a catheter interlock system which includes a blood access device having at least one conduit adapted for insertion in the circulatory system of a living body. A housing of the device has an open end, and the interior of the housing is in fluid communication with the conduit. A coaxially rotatable valve body is provided in the housing, and the valve body has an axial bore in its outer end. A cannula receptacle is inserted in an affixed relation in the axial bore, and a flange is provided on the cannula receptacle that overlies the outer end of the valve body. A catheter tip is adapted for insertion in and engagement with the cannula receptacle. A lug on the outer surface of the catheter tip extends outwardly at right angles to the axis of the catheter, and a cap is provided over the open end of the housing, valve body and cannula receptacle. The cap is of the screw type and has a shoulder for bearing against the flange of the cannula receptacle to provide compression to retain the valve body in a rotatively seated condition in the housing. The cap also is provided with a generally circular orifice and a key slot adjacent the circumference of the orifice. The cap also is provided with a circumferential slot in the inner wall thereof adjoining the key slot. The key slot serves as a passageway for the lug to enter the circumferential slot. The lug secures the position of the catheter after insertion thereof in the cannula receptacle through the cap and after rotation of the catheter to engage the lug in the circumferential slot. This prevents an inadvertent removal of the catheter when the valve is open.

While the invention has been described in connection with a preferred embodiment, alternatives, modifications, and variations may be apparent to those skilled in the art in view of the foregoing description. Accordingly, it is intended to embrace all such alternatives, modifications, and variations as fall within the spirit and scope of the appended claims.

What is claimed is:

1. A catheter interlock system comprising a blood access device having at least one conduit adapted for insertion in the circulatory system of a living body; a housing having an open end, the interior of said housing being in fluid communication with the conduit; a coaxially rotatable valve body in said housing, said valve body having an axial bore in its outer end; a cannula receptacle inserted and affixed in the axial bore of said valve body, said receptacle having a flange overlying the outer ends of said valve body; a catheter tip adapted for insertion in and engagement with said cannula receptacle; a lug on the outer surface of said catheter tip extending outwardly at right angles to the axis of the catheter; and a cap over the open end of said housing, valve body and cannula receptacle, said cap being of the screw type and having a shoulder for bearing against the flange of the cannula receptacle to provide compression to retain said valve body in a rotatively seated condition in said housing, said cap being provided with a generally circular orifice and a key slot adjacent the circumference of the orifice and said cap having a circumferential slot in the inner wall thereof adjoining said key slot, said key slot serving as a passageway for said lug to enter said circumferential slot and said lug securing the position of the catheter after insertion thereof in said cannula receptacle and after rotation of the catheter to engage the lug in said circumferential slot.

2. A catheter interlock system in accordance with claim 1 wherein said blood access device is a duo-directional device provided with means for permitting simultaneous withdrawal from and return of blood to the circulatory system.

3. A catheter interlock system in accordance with claim 1 wherein said blood access device is a uni-directional device having means to permit fluid to pass only in one direction at a time either outwardly from or inwardly to the circulatory system.

4. A system in accordance with claim 1 wherein said catheter tip includes a pair of flutes in its outer surface and wherein said cannula receptacle includes a pair of longitudinal guides on its inner surface located to engage the flutes of the catheter when the catheter is inserted therethrough, whereby the catheter after being inserted in said valve body may be utilized for rotating said valve body to open and close the valve.

5. A system in accordance with claim 4 wherein said cannula receptacle includes a pair of grooves in its outer surface and said valve body includes a pair of grooves on its inner surface located to oppose the pair of grooves in the cannula receptacle and in such opposition forming a cylindrical cavity therebetween, and wherein said system further includes an interlock rod disposed in each cylindrical cavity formed by the opposing grooves.

* * * * *